US00PP25527P3

(12) United States Plant Patent

Klemm et al.

(10) Patent No.: US PP25,527 P3

(45) Date of Patent: May 5, 2015

(54) *LOBELIA* PLANT NAMED 'KLELE12094'

(50) Latin Name: *Lobelia erinus*
Varietal Denomination: KLELE12094

(71) Applicant: Klemm+Sohn GmbH & Co. KG, Stuttgart (DE)

(72) Inventors: Nils Klemm, Stuttgart (DE); Guido von Tubeuf, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 168 days.

(21) Appl. No.: 13/986,952

(22) Filed: Jun. 18, 2013

(65) Prior Publication Data

US 2014/0373242 P1 Dec. 18, 2014

(51) Int. Cl.
*A01H 5/00* (2006.01)

(52) U.S. Cl.
USPC ..... Plt./451

(58) Field of Classification Search
USPC ..... Plt./451
See application file for complete search history.

(56) References Cited

PUBLICATIONS

PLUTO Plant Variety database Jan. 14, 2015.*

* cited by examiner

*Primary Examiner* — Annette Para

(74) *Attorney, Agent, or Firm* — Barbara Campbell; James M. Weatherly; Cochran Freund & Young LLC

(57) ABSTRACT

A new *Lobelia* plant particularly distinguished by blue flowers with no eyes and a compact and upright growth habit, is disclosed.

1 Drawing Sheet

Genus and species: *Lobelia erinus.*
Variety denomination: 'KLELE12094'.

BACKGROUND OF THE NEW PLANT

The present invention comprises a new and distinct variety of *Lobelia,* botanically known as *Lobelia erinus,* and hereinafter referred to by the variety name 'KLELE12094'. 'KLELE12094' originated from a controlled cross conducted in September 2008 in Stuttgart, Germany between the proprietary female *Lobelia* variety 'B 067' (unpatented) having medium vigor and the male *Lobelia* variety TECHNO HEAT 'Upright Blue' (patent status unknown), having light blue flowers with eyes.

The seeds from the cross were sown and plants were grown in a greenhouse for evaluation, where an individual plant designated 'KLELE12094' was selected from the group of plants in May 2009, having blue flowers with no eyes and compact growth habit. In May 2009 'KLELE12094' was first vegetatively propagated by tissue culture and vegetative cuttings. 'KLELE12094' was found to reproduce true to type in successive generations of asexual propagation via tissue culture and vegetative cuttings.

CROSS REFERENCE TO RELATED APPLICATIONS

Plant Breeder's Rights for 'KLELE12094' were applied for in Canada on Feb. 8, 2013, Application No. 13-7918. 'KLELE12094' has not been made publicly available or sold more than one year prior to the filing date of this application.

SUMMARY

The following are the most outstanding and distinguishing characteristics of this new variety when grown under normal horticultural practices in Stuttgart, Germany.

1. Blue flowers with no eyes; and
2. A compact vigor and upright growth habit.

DESCRIPTION OF THE PHOTOGRAPH

This new *Lobelia* plant is illustrated by the accompanying photograph which shows the plant's overall plant habit including form, foliage, and flowers. The photograph is of a four-month-old plant grown in a greenhouse in Stuttgart, Germany in May 2012. The colors shown are as true as can be reasonably obtained by conventional photographic procedures.

DESCRIPTION OF THE NEW VARIETY

The following detailed descriptions set forth the distinctive characteristics of 'KLELE12094'. The data which define these characteristics were collected from asexual reproductions carried out in Stuttgart, Germany. Data was collected on three-month-old plants grown in a greenhouse in Stuttgart, Germany in April 2013. Color references are to The R.H.S. Colour Chart of The Royal Horticultural Society of London (R.H.S.), $5^{th}$ edition (2007).

Classification:

*Family.*—Campanulaceae.
*Botanical.*—*Lobelia erinus.*
*Common.*—*Lobelia.*
*Designation.*—'KLELE12094'.
*Parentage.*—Female parent: The proprietary *Lobelia* variety 'B 067' (unpatented). Male parent: The *Lobelia* variety TECHNO HEAT 'Upright Blue' (patent status unknown).

Growth:

*Growth and branching habit.*—Compact and upright.
*Form.*—Rounded.

*Height* (*measured from top of soil including flowers*).—8.0 cm.

*Width* (*horizontal plant diameter including any flowers*).—15.0 cm.

*Outdoor plant performance.*—Very good.

*Time to produce a finished flowering plant.*—7 weeks.

*Time to initiate and develop roots.*—2 weeks.

*Root description.*—Fine, white.

Leaves:

*Arrangement.*—Alternate.

*Color, immature and mature leaf.*—Upper surface: RHS 137A. Lower surface: RHS 138C.

*Length.*—3.0 cm to 4.5 cm.

*Width.*—0.5 cm to 1.5 cm.

*Shape.*—Elliptical to lanceolate (upper leaves are more lanceolate).

*Apex.*—Obtuse.

*Base.*—Acute.

*Margin.*—Serrate (lanceolate leaves partly with entire margins).

*Texture* (*both upper and lower surfaces*).—Hairy.

*Venation type.*—Pinnate.

Stems:

*Length.*—5.0 cm to 7.0 cm.

*Diameter.*—0.2 cm to 0.3 cm.

*Internode length.*—0.3 cm to 1.7 cm.

*Color.*—RHS 139B.

*Anthocyanin.*—Absent.

*Texture and appearance.*—Hairy.

*Peduncle.*—Length: 2.0 cm to 2.5 cm. Diameter: 0.05 cm. Texture: Smooth. Color: RHS 139B.

Flower buds:

*Shape.*—Inverse drop.

*Length.*—About 0.8 cm.

*Diameter.*—0.25 cm.

*Color* (*at tight bud*).—RHS N79B.

Inflorescence:

*Blooming habit.*—Continuous.

*Lastingness of individual blooms on the plant.*—About 1 week.

*Fragrance.*—Absent.

*Inflorescence type.*—Raceme.

*Quantity of flowers and buds per flowering branch.*—8 to 12.

Flowers:

*Flower diameter.*—2.0 cm.

*Flower height.*—0.8 cm.

*Mature flower.*—Upper lobe: Color upper surface: RHS 99C. Color lower surface: RHS 93C. Length: 0.6 cm. Width: 0.2 cm. Shape: Lanceolate. Apex: Acute. Margin: Entire. Texture, both upper and lower surfaces: Smooth. Lower lobes: Color, upper surface: RHS 99C. Color, lower surface: RHS 97D towards the bottom, RHS 96D towards the tip. Length: 1.0 cm. Width: 0.7 cm. Shape: Obovate. Apex: Obtuse. Margin: Entire. Texture, both upper and lower surfaces: Smooth. Corolla tube: Color inside: RHS NN155D (White) with RHS 96D blue pattern. Color outside: RHS NN155D (White). Tube length: 0.8 cm. Diameter: 0.3 cm. Calyx: Length: 0.3 cm fused part and 1.0 cm for non-fused part. Diameter: 0.1 cm. Shape: Funnel, star-shaped (sepals are fused in lower half). Apex: Acute. Texture: Hairy. Color: RHS 137A.

Reproductive organs:

*Stamens.*—Quantity: 5. Filament length: 0.5 cm. Filament color: RHS 96C. Anther color: RHS N77C. Anther length: 0.2 cm. Anther width: 0.1 cm. Pollen amount: Moderate. Pollen color: Greyed-yellow.

*Pistils.*—Quantity per flower: 1. Pistil length: 0.7 cm. Stigma color: RHS N92A (Greyed-violet). Stigma shape: Rounded, two-sided. Style length: 0.6 cm. Style color: RHS 142C. Ovary color: RHS 142B.

Fruit and seed set: Fruit and seed set observed later in the year.

Disease and pest/insect resistance: No disease and pest/insect resistance observed.

COMPARISON WITH PARENTAL LINES AND KNOWN VARIETY

'KLELE12094' is a distinct variety of *Lobelia* having compact vigor and an upright growth habit and is distinguished from its parents as described in Table 1.

TABLE 1

Comparison with Parental Lines

| Characteristic | 'KLELE12094' | Female Parent 'B 067' | Male Parent TECHNO HEAT 'Upright Blue' |
|---|---|---|---|
| Flower color | Blue (no eye) | | Light blue with an eye |
| Vigor | Compact | Medium | |

'KLELE12094' KLELE12094' is a distinct variety of *Lobelia* having compact vigor and an upright growth habit is most similar to the commercial *Lobelia* variety MAGADI 'Compact Blue' (patent status unknown). Differences between the varieties are described in Table 2.

TABLE 2

Comparison with Similar Variety

| Characteristic | 'KLELE12094' | MAGADI 'Compact Blue' |
|---|---|---|
| Vigor | Compact | Medium |
| Flower color | Blue | Light blue |

We claim:

1. A new and distinct variety of *Lobelia* plant designated 'KLELE12094' as shown and described herein.

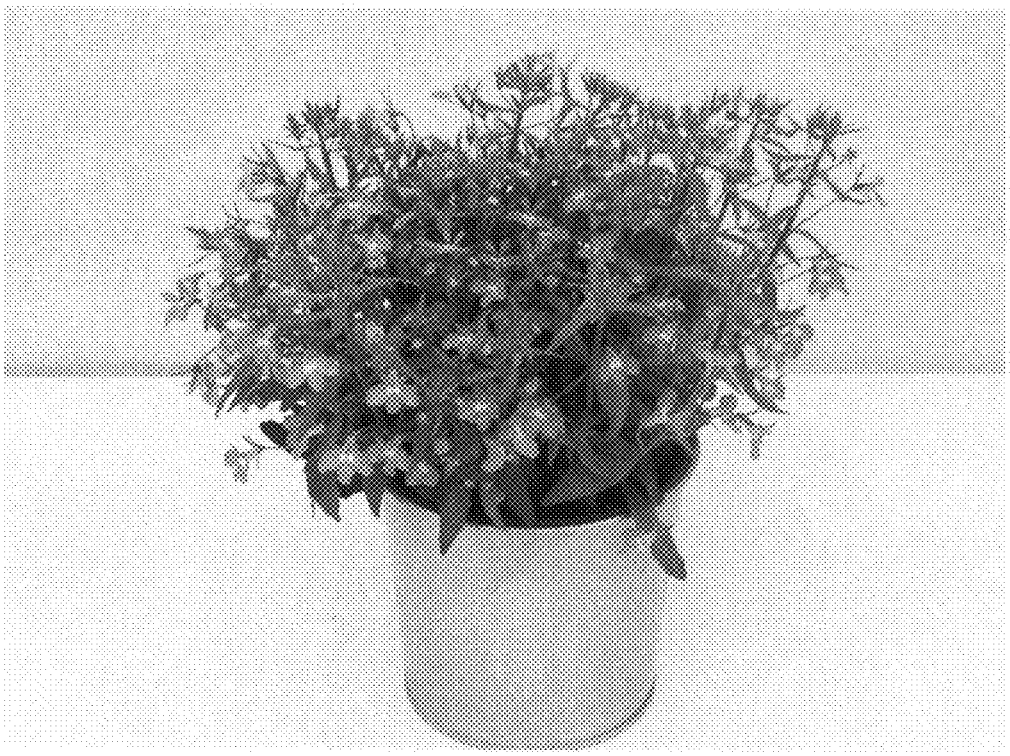

* * * * *